United States Patent
Hobart et al.

(10) Patent No.: US 6,743,221 B1
(45) Date of Patent: Jun. 1, 2004

(54) LASER SYSTEM AND METHOD FOR TREATMENT OF BIOLOGICAL TISSUES

(76) Inventors: James L. Hobart, 25111 Tepa Way, Los Altos, CA (US) 94022; Daniel K. Negus, 305 Spagnoli Ct., Los Altos, CA (US) 94022; Daniel Paul Joseph, 24 Ridgemoor Dr., Clayton, MO (US) 63105; Peter Nigel Allen, 9232 Klemetson Dr., Pleasanton, CA (US) 94588

( * ) Notice: Subject to any disclaimer, the term of this patent is extended or adjusted under 35 U.S.C. 154(b) by 11 days.

(21) Appl. No.: 10/097,555

(22) Filed: Mar. 12, 2002

Related U.S. Application Data

(60) Provisional application No. 60/275,828, filed on Mar. 13, 2001.

(51) Int. Cl.$^7$ ............................................. A61B 18/18
(52) U.S. Cl. .............................. 606/4; 128/898; 606/10
(58) Field of Search ............................ 606/2–6, 10–12; 128/898

(56) References Cited

U.S. PATENT DOCUMENTS

| | | |
|---|---|---|
| 2,702,552 A | 2/1955 | Moodie |
| 2,715,315 A | 8/1955 | Giardini |
| 3,307,553 A | 3/1967 | Liebner |
| 3,466,111 A | 9/1969 | Ring |
| 3,538,919 A | 11/1970 | Meyer |
| 3,596,514 A | 8/1971 | Mefferd et al. |
| 3,693,623 A | 9/1972 | Harte et al. |
| 3,720,213 A | 3/1973 | Hobart et al. |
| 3,783,407 A | 1/1974 | Mefferd et al. |

(List continued on next page.)

FOREIGN PATENT DOCUMENTS

| | | | |
|---|---|---|---|
| DE | 195 21 003 C1 | 8/1996 | ............ A61B/17/36 |
| EP | 0 073 617 A1 | 3/1983 | ............ A61C/1/08 |
| EP | 0 164 751 A2 | 12/1985 | ............ H01S/3/097 |
| EP | 0 714 642 A1 | 6/1996 | ............ A61F/2/10 |
| EP | 0 755 698 A2 | 1/1997 | ............ A61N/5/06 |
| EP | 1 057 454 A2 | 12/2000 | ............ A61B/18/20 |

(List continued on next page.)

OTHER PUBLICATIONS

Brigitte Dreno, MD., et al., "The Benefit of Chilling in Argon–Laser Treatment of Port–Wine Stains," vol. 75, No. 1, Chilling in Argon–Laser Treatment, pp. 42–45.

Barbara A. Gilchrest.et al., "Chilling Port Wine Stains Improves the Response to Argon Laser Therapy," Plastic and Reconstructive Surgery, vol. 69, No. 2, 1982, pp. 278–283.

Akira Yanai, M.D., et al., "Argon Laser Therapy of Port–Wine Stains: Effects and Limitations," vol. 75, No. 4, Apr. 1985, pp. 520–525.

(List continued on next page.)

*Primary Examiner*—Michael Peffley
(74) *Attorney, Agent, or Firm*—Haverstock & Owens LLP

(57) ABSTRACT

A system for and method of performing laser assisted surgery is disclosed. Laser radiation is preferably delivered to a target area of tissue using a Er:YAG laser source. The laser radiation is delivered to the target area in bursts of laser radiation comprising sets of laser pulses. The bursts of laser radiation are preferably delivered to the target area at a repetition rate in a range of 10 to 40 Hz and with sufficient pulse fluences to cut and/or dissect. In accordance with a preferred embodiment, interchangeable and flexible endoprobes are configured with shield features. The shield features control the emission of laser radiation from the optical fiber while bending the flexible probes allow surgeons to access a range of approach angles for the laser treatment of biological tissue enclosed or within a cavity of a body. The probes can also be configured with mechanical cutters or other structures which allow for the mechanical manipulation of tissue during laser treatment. The system for and method of performing laser assisted surgery is particularly well suited for treating fibrous and/or fibro-vascular membranes (FVMs) on ophthalmic tissue during vitreoretinal surgery.

21 Claims, 8 Drawing Sheets

U.S. PATENT DOCUMENTS

| | | |
|---|---|---|
| 3,821,510 A | 6/1974 | Muncheryan |
| 3,834,391 A | 9/1974 | Block |
| 3,854,153 A | 12/1974 | Fadler et al. |
| 3,868,592 A | 2/1975 | Yarborough et al. |
| 3,873,941 A | 3/1975 | Yarborough et al. |
| 3,900,034 A | 8/1975 | Katz et al. |
| 3,934,210 A | 1/1976 | Yarborough et al. |
| 3,967,627 A | 7/1976 | Brown |
| 3,973,825 A | 8/1976 | Starkweather |
| 3,995,166 A | 11/1976 | Hobart et al. |
| 4,006,299 A | 2/1977 | Grafton |
| 4,071,031 A | 1/1978 | Lowman |
| 4,122,853 A * | 10/1978 | Smith .............................. 606/4 |
| 4,140,130 A | 2/1979 | Storm, III |
| 4,143,660 A | 3/1979 | Malyshev et al. |
| 4,149,529 A | 4/1979 | Copeland et al. |
| 4,150,342 A | 4/1979 | Johnston, Jr. et al. |
| 4,174,154 A | 11/1979 | Kawasaki |
| 4,185,633 A | 1/1980 | Prozorov et al. |
| 4,240,431 A | 12/1980 | Komiya |
| 4,274,703 A | 6/1981 | Fisli |
| 4,276,520 A | 6/1981 | Rosenberg |
| 4,276,779 A | 7/1981 | Davis, Jr. |
| 4,309,998 A * | 1/1982 | Aron nee Rosa et al. ....... 606/3 |
| 4,313,093 A | 1/1982 | Suenaga et al. ........ 331/94.5 D |
| 4,329,997 A | 5/1982 | de Yampert et al. ......... 128/402 |
| 4,373,816 A | 2/1983 | Laib .............................. 356/375 |
| 4,378,600 A | 3/1983 | Hobart ........................ 372/62 |
| 4,381,007 A | 4/1983 | Doss ....................... 128/303.1 |
| RE31,279 E | 6/1983 | Mefferd et al. |
| 4,388,924 A | 6/1983 | Weissman et al. ....... 128/303.1 |
| 4,391,275 A * | 7/1983 | Fankhauser et al. ........... 606/4 |
| 4,408,602 A | 10/1983 | Nakajima ................. 128/303.1 |
| 4,461,294 A | 7/1984 | Baron ...................... 128/303.1 |
| 4,473,074 A | 9/1984 | Vassiliadis ............... 128/303.1 |
| 4,500,996 A | 2/1985 | Sasnett et al. ................. 372/19 |
| 4,503,854 A | 3/1985 | Jako ........................ 128/303.1 |
| 4,516,564 A | 5/1985 | Koiso et al. ................. 126/263 |
| 4,538,181 A | 8/1985 | Taylor ......................... 358/208 |
| 4,545,657 A | 10/1985 | Sunago ....................... 350/600 |
| 4,559,942 A | 12/1985 | Eisenberg ................... 128/303 |
| 4,566,107 A | 1/1986 | Kitaura et al. ................. 372/38 |
| 4,601,037 A * | 7/1986 | McDonald ................... 372/25 |
| 4,608,978 A | 9/1986 | Rohr ......................... 128/303.1 |
| 4,608,979 A | 9/1986 | Breidenthal et al. ..... 128/303.1 |
| 4,617,926 A | 10/1986 | Sutton ..................... 128/303.1 |
| 4,660,798 A | 4/1987 | Kinoshita ................... 248/648 |
| 4,662,730 A | 5/1987 | Outwater et al. ........... 351/212 |
| 4,665,913 A | 5/1987 | L'Esperance, Jr. ....... 128/303.1 |
| 4,672,969 A | 6/1987 | Dew .......................... 128/397 |
| 4,684,222 A | 8/1987 | Borrelli et al. ............. 350/420 |
| 4,733,660 A | 3/1988 | Itzkan ..................... 128/303.1 |
| 4,753,503 A | 6/1988 | Day et al. ................... 350/3.71 |
| 4,761,047 A | 8/1988 | Mori ......................... 350/96.1 |
| 4,785,456 A | 11/1988 | Kaplan ......................... 372/38 |
| 4,791,927 A | 12/1988 | Menger ................... 128/303.1 |
| 4,819,669 A | 4/1989 | Politzer ....................... 132/200 |
| 4,852,115 A | 7/1989 | Viherkoski .................... 372/92 |
| 4,856,513 A | 8/1989 | Muller ................... 128/303.1 |
| 4,864,578 A | 9/1989 | Proffitt et al. ................. 372/20 |
| 4,871,252 A | 10/1989 | Beni et al. ................... 356/347 |
| 4,887,019 A | 12/1989 | Reis et al. ................... 350/6.1 |
| 4,887,894 A | 12/1989 | Gluzerman et al. ........ 350/636 |
| 4,896,015 A | 1/1990 | Taboada et al. ....... 219/121.78 |
| 4,915,484 A | 4/1990 | Yamamoto ................. 350/420 |
| 4,939,739 A | 7/1990 | Hobart et al. ............... 372/107 |
| 4,941,093 A | 7/1990 | Marshall et al. ....... 364/413.01 |
| 4,949,358 A | 8/1990 | Kantorski et al. ............. 372/94 |
| 4,963,143 A | 10/1990 | Pinnow ....................... 604/14 |
| 4,971,411 A | 11/1990 | Takanashi ................. 350/6.5 |
| 5,000,752 A | 3/1991 | Hoskin et al. .................. 606/9 |
| 5,023,886 A | 6/1991 | Hobart et al. .................. 372/99 |
| 5,033,061 A | 7/1991 | Hobart et al. ................ 372/107 |
| 5,046,184 A | 9/1991 | Chee et al. |
| 5,052,017 A | 9/1991 | Hobart et al. .................. 372/99 |
| 5,055,048 A | 10/1991 | Vassiliadis et al. ......... 433/215 |
| 5,057,104 A | 10/1991 | Chess ............................. 606/9 |
| 5,059,192 A | 10/1991 | Zaias ............................. 606/9 |
| 5,061,062 A | 10/1991 | Schneiter ...................... 356/1 |
| 5,098,426 A | 3/1992 | Sklar et al. ..................... 606/5 |
| 5,123,028 A | 6/1992 | Hobart et al. ................. 372/95 |
| 5,123,845 A | 6/1992 | Vassiliadis et al. ......... 433/215 |
| 5,125,922 A | 6/1992 | Dwyer et al. |
| 5,125,923 A | 6/1992 | Tanner et al. ................. 606/10 |
| 5,128,509 A | 7/1992 | Black et al. ........... 219/121.76 |
| 5,140,606 A | 8/1992 | Yarborough et al. .......... 372/64 |
| 5,152,759 A | 10/1992 | Parel et al. ..................... 606/5 |
| 5,168,386 A | 12/1992 | Galbraith .................... 359/215 |
| 5,182,857 A | 2/1993 | Simon ....................... 30/34.05 |
| 5,190,032 A | 3/1993 | Zacoi .......................... 128/400 |
| 5,198,926 A | 3/1993 | Sheinis et al. .............. 359/356 |
| 5,207,576 A | 5/1993 | Vassiliadis et al. ......... 433/215 |
| 5,210,398 A | 5/1993 | Metlitsky ................... 235/462 |
| 5,226,907 A | 7/1993 | Tankovich ................. 606/133 |
| 5,227,910 A | 7/1993 | Khattak ..................... 359/211 |
| 5,269,778 A | 12/1993 | Rink et al. |
| 5,275,564 A | 1/1994 | Vassiliadis et al. ......... 433/226 |
| 5,282,797 A | 2/1994 | Chess ............................. 606/9 |
| 5,292,320 A | 3/1994 | Brown et al. ................. 606/15 |
| 5,300,066 A | 4/1994 | Manoukian et al. .......... 606/15 |
| 5,312,398 A | 5/1994 | Hobart et al. ................. 606/14 |
| 5,335,242 A | 8/1994 | Hobart et al. ................. 372/95 |
| 5,344,418 A | 9/1994 | Ghaffari ........................ 606/9 |
| 5,359,669 A | 10/1994 | Shanley et al. ................ 382/6 |
| 5,360,447 A | 11/1994 | Koop .......................... 623/15 |
| 5,375,132 A | 12/1994 | Connors et al. .............. 372/34 |
| 5,405,368 A | 4/1995 | Eckhouse .................... 607/88 |
| 5,411,502 A | 5/1995 | Zair ............................. 606/10 |
| 5,413,555 A | 5/1995 | McMahan ..................... 606/4 |
| 5,421,819 A | 6/1995 | Edwards et al. .............. 604/22 |
| 5,423,801 A | 6/1995 | Marshall et al. ............... 606/5 |
| 5,425,727 A | 6/1995 | Koziol .......................... 606/5 |
| 5,425,728 A | 6/1995 | Tanovich ....................... 606/9 |
| 5,426,662 A | 6/1995 | Mefferd et al. ............... 372/99 |
| 5,464,013 A | 11/1995 | Lemelson ................. 128/653.1 |
| 5,474,549 A | 12/1995 | Ortiz et al. .................... 606/9 |
| 5,480,396 A | 1/1996 | Simon et al. .................. 606/4 |
| 5,486,172 A | 1/1996 | Chess ........................... 606/20 |
| 5,520,679 A | 5/1996 | Lin ............................... 606/5 |
| 5,522,813 A * | 6/1996 | Trelles ......................... 606/2 |
| 5,531,470 A | 7/1996 | Townsend ................. 280/730.2 |
| 5,531,740 A | 7/1996 | Black ............................. 606/9 |
| 5,540,676 A | 7/1996 | Freiberg ........................ 606/3 |
| 5,546,214 A | 8/1996 | Black et al. ................. 359/203 |
| 5,582,752 A | 12/1996 | Zair ....................... 219/121.85 |
| 5,585,698 A | 12/1996 | Langhans et al. ....... 315/200 A |
| 5,595,568 A | 1/1997 | Anderson et al. .............. 606/9 |
| 5,611,795 A | 3/1997 | Slatkine et al. ................ 606/9 |
| 5,618,285 A | 4/1997 | Zair ............................. 606/10 |
| 5,620,435 A | 4/1997 | Belkin et al. .................. 606/4 |
| 5,620,478 A | 4/1997 | Eckhouse .................... 607/88 |
| 5,624,437 A | 4/1997 | Freeman et al. .............. 606/12 |
| 5,626,631 A | 5/1997 | Eckhouse .................... 607/88 |
| 5,637,850 A | 6/1997 | Honda ........................ 235/454 |
| 5,642,287 A | 6/1997 | Sotiropoulos et al. . 364/474.08 |
| 5,643,334 A | 7/1997 | Echhouse et al. ............. 607/88 |
| 5,645,550 A | 7/1997 | Hohla ......................... 606/108 |
| 5,651,784 A | 7/1997 | Klopotek ....................... 606/5 |
| 5,655,547 A | 8/1997 | Karni .......................... 128/898 |
| 5,659,563 A | 8/1997 | Reed et al. .................. 372/101 |
| 5,662,643 A | 9/1997 | Kung et al. .................... 606/3 |

| | | | |
|---|---|---|---|
| 5,662,644 A | 9/1997 | Swor | 606/9 |
| 5,735,844 A | 4/1998 | Anderson et al. | 606/9 |
| 5,738,677 A * | 4/1998 | Colvard et al. | 606/4 |
| 5,756,131 A | 5/1998 | Roustaei et al. | 235/462 |
| 5,769,787 A | 6/1998 | Lemelson | 600/407 |
| 5,770,847 A | 6/1998 | Olmstead | 235/46.2 |
| 5,781,574 A | 7/1998 | Conners et al. | 372/35 |
| 5,782,822 A | 7/1998 | Telfair et al. | 606/5 |
| 5,783,798 A | 7/1998 | Abraham | 219/121.73 |
| 5,814,803 A | 9/1998 | Olmstead et al. | 235/462 |
| 5,814,827 A | 9/1998 | Katz | 250/556 |
| 5,846,080 A | 12/1998 | Schneider | 433/215 |
| 5,849,006 A | 12/1998 | Frey et al. | 606/5 |
| 5,865,830 A | 2/1999 | Parel et al. | 606/5 |
| 5,868,731 A | 2/1999 | Budnik et al. | 606/9 |
| 5,883,658 A | 3/1999 | Schubert et al. | 347/258 |
| 5,900,963 A | 5/1999 | Li et al. | 359/205 |
| 5,931,848 A | 8/1999 | Saadat | 606/167 |
| 5,933,268 A | 8/1999 | Li et al. | 359/207 |
| 5,938,657 A | 8/1999 | Assa et al. | 606/9 |
| 5,941,893 A | 8/1999 | Saadat | 606/180 |
| 5,984,915 A * | 11/1999 | Loeb et al. | 606/9 |
| 5,997,531 A | 12/1999 | Loeb et al. | 606/13 |
| 6,066,127 A | 5/2000 | Abe | 606/2 |
| RE36,872 E | 9/2000 | Zair | |
| 6,162,213 A | 12/2000 | Stewart | 606/10 |
| 6,228,075 B1 | 5/2001 | Furumoto | 606/9 |
| 6,228,076 B1 | 5/2001 | Winston et al. | 606/11 |
| 6,267,771 B1 | 7/2001 | Tanovich et al. | 606/131 |
| 6,270,222 B1 | 8/2001 | Herpst | 359/511 |
| 6,471,691 B1 * | 10/2002 | Kobayashi et al. | 606/4 |
| 6,524,330 B1 * | 2/2003 | Khoobehi et al. | 607/89 |
| 6,613,042 B1 * | 9/2003 | Tankovich et al. | 606/10 |
| 2001/0007068 A1 | 7/2001 | Ota et al. | 606/9 |
| 2001/0029364 A1 | 10/2001 | Almeida | 606/9 |
| 2003/0032949 A1 * | 2/2003 | Schuele et al. | 606/4 |
| 2003/0078567 A1 * | 4/2003 | Dorin et al. | 606/4 |

FOREIGN PATENT DOCUMENTS

| | | | |
|---|---|---|---|
| JP | 56-166123 | 12/1981 | A61K/45/00 |
| WO | WO 86/02783 | 5/1986 | H01S/3/08 |
| WO | WO 92/18057 | 10/1992 | A61B/17/22 |
| WO | WO 93/03521 | 2/1993 | H01S/3/08 |
| WO | WO 95/15725 | 6/1995 | A61B/17/41 |
| WO | WO 96/34566 * | 11/1996 | |
| WO | WO 96/41577 | 12/1996 | |

OTHER PUBLICATIONS

R. Rox Anderson et al., "Selective Photothermolysis: Precise Microsurgery by Selective Absorption of Pulsed Radiation," vol. 220, Apr. 1983, pp. 524–527.

Rory C.D. Herdman et al., "An in vitro comparison of the Erbium: YAG laser and the carbon dioxide laser in laryngeal surgery," vol. 107, Oct. 1993, pp. 908–911.

Joseph T. Walsh, Jr. et al., "Pulsed CO2 Laser Tissue Ablation: Measurement of the Ablation Rate," Laser in Surgery and Medicine, 1998, pp. 264–275.

Joseph T. Walsh, Jr. et al., "Effect of Tissue Type and Pulse Duration on Thermal Damage," 1998 Alan R. Liss, Inc., pp. 110–118.

Joseph T. Walsh, Jr. et al., "Pulsed CO2 Laser Ablation of Tissue: Effect of Mechanical Properties," Transaction on Biomedical Engineering, vol. 36, No. 12, Dec. 1989, pp. 1195–1201.

E. Victor Ross, MD., et al., "Effects of Heterogeneous Absorption of Laser Radiation in Biotissue Ablation: Characterization of Ablation of Fat with a Pulsed CO2 Laser," Laser in Surgery and Medicine, 1997, pp. 59–64.

"Erbium Laser Gaining Popularity for Cosmetic Applications", Medical Laser Report, Nov. 1996, pp. 2–3.

U. Hohenleutner et al., "Fast and Effective Skin Ablation with an Er:YAG Laser: Determination of Ablation Rates and Thermal Damages Zones," Laser in Surgery and Medicine 20, 1997, pp. 242–247.

Brigita Drnovsek–Olup et al., "Use of Er:YAG Laser for Benign Skin Disorders," Laser in Surgery and Medicine 21, 1997, pp. 13–19.

Leon Goldman, MD., et al., "Replica Microscopy and Scanning Electron Microscopy of Laser Impacts on the Skin," The Journal of Investigative Dermatology, vol. 52, No. 1, pp. 18–24.

Melanie C. Grossman M.D., et al., "Damage to hair follicles by normal–mode ruby laser pulses," Journal of the American Academy of Dermatology, Dec. 1996, pp. 889–894.

Luigi L. Polla MD., et al., "Melanosomes Are a Primary Target of Q–Switched Ruby Laser Irradiation in Guinea Pig Skin," The Society for Investigative Dermatology, Inc., vol. 89, No. 3, 1987, pp. 281–286.

"The Journal of Investigative Dermatology," Apr. 1987, vol. 88, No. 4, pp. 523.

M. Douglas Gossman, MD., et al., "Prospective Evaluation of the Argon Laser in the Treatment of Trichiasis," Mar. 1992, vol. 23, No. 3, 183–187.

"Selective Photothermolysis: Precise Microsurgery by Selective Absorption of Pulsed Radiation," Science, vol. 220, Apr. 1983, pp. 524–527.

R. Rox Anderson et al., "The Optics of Human Skin," The Journal of Investigative Dermatology 77, 1981, pp. 13–19.

Leon Goldman M.D., et al., "Treatment of Basal Cell Epithelioma by Laser Radiation," Epithelioma–Goldman & Wilson, 1961, vol. 189, No. 10, pp. 773–775.

Leon Goldman MD., et al., "Laser Action at the Cellular Level," Multidiscipline Research Forum, JAMA, Nov. 7, 1996, vol. 198, No. 6, pp. 641–644.

Leon Goldman MD., et al., "Biomedical Aspects of Lasers" JAMA, Apr. 20, 1964, vol. 188, No. 3, pp. 302–306.

Leon Goldman MD., et al., "Effect of the Laser Beam on the Skin," Preliminary Report, 2 pgs.

Leon Goldman MD., et al., "Effect of the Laser Beam on the Skin," III. Exposure of Cytological Preparations, pp. 247–251.

"Pathology of the Effect of the Laser Beam on the Skin," Nature, Mar. 2, 1963, vol. 197, pp. 912–914.

"Preliminary Investigation of Fat Embolization from Pulsed Ruby Laser Impacts of Bone," Nature, vol. 221, Jan. 1969, pp. 361–363.

Leon Goldman MD., et al., "Radiation from a Q–Switched Ruby Laser: Effect of Repeated Impacts of Power Output of 10 Megawatts on a Tattoo of Man," pp. 69–71.

Roland Kaufmann MD., et al., "Pulsed Er:YAG– and 308 nm UV–Excimer Laser: An In Vitro and In Vivo Study of Skin–Ablative Effects," Laser in Surgery and Medicine 9, 1989, pp. 132–140.

A.D. Zweig et al., "A Comparative Study of Laser Tissue Interaction of 2.94 $\mu$m and 10.6 $\mu$m," Appl. Phys. B 47, 1998, pp. 259–265.

B.R. Burkhardt MD., et al., "Are More Passes Better? Safety versus Efficacy with Pulsed CO2 Laser," Cosmetic, Nov. 1997, pp. 1531–1534.

Roland Kaufmann MD., et al., "Cutting and Skin–Ablative Properties of Pulsed Mid–Infrared Laser Surgery," 1994, pp. 112–118.

Joseph T. Walsh, Jr., MD., et al., "Er:YAG Laser Ablation of Tissue: Measurement of Ablation Rate," Laser in Surgery and Medicine 9, 1989, pp. 327–337.

Joseph T. Walsh, Jr., MD., et al., "Er:YAG Laser Ablation of Tissue: Effect of Pulse Duration and Tissue Type on Thermal Damage," Laser in Surgery and Medicine p. 1989, pp. 314–326.

Roland Kaufmann MD., "Pulsed 2.94–$\mu$m erbium–YAG Laser Skin Ablation Experimental Results and First Clinical Application," 1990, 15, pp. 389–393.

Raimund Hibst et al., "Effects of Laser Parameters on Pulsed Er–YAG Laser Skin Ablation<" Lasers in Medical Science, vol. 6:9391, 1991, pp. 391–397.

* cited by examiner

LASER SYSTEM AND METHOD FOR TREATMENT OF BIOLOGICAL TISSUES

RELATED APPLICATION(S)

This Patent Application claims priority under 35 U.S.C. 119 (e) of the co-pending U.S. Provisional Patent Application, Serial No. 60/275,828, filed Mar. 13, 2001, and entitled "MEDICAL LASER SYSTEM". The Provisional Patent Application, Serial No. 60/275,828, filed Mar. 13, 2001, and entitled "MEDICAL LASER SYSTEM" is also hereby incorporated by reference.

FIELD OF THE INVENTION

The present invention relates to systems for and methods of treating biological tissue and vascular biological tissue. More specifically, this invention relates to systems for and methods of treating biological tissues and vascular tissues with laser radiation that are within an enclosed space or within a cavity of the body, such as vascular ophthalmic tissues.

BACKGROUND OF THE INVENTION

Proliferative diabetic retinopathy (PDR) and proliferative vitreoretinopathy (PVR) are the most common causes of permanent or severe visual loss associated with retinal detachment. At the core of visual loss in both of these diseases is the growth of fibrous and/or fibro-vascular membranes, referred to generally herein as FVMs. The FVMs grow or develop on or near the surface of the retina. The growth of FVMs causes tractional retinal detachments, combined tractional-rhegmatogenous retinal detachments, and vitreous hemorrhages. Prior to the development of vitrectomy, severe cases of proliferative vitreoretinopathy that underwent conventional scleral buckle failed to reattach the retina in up to 70% of cases (Yoshida et al., 1984; Grizzard and Hilton, 1982). With the advent of photocoagulation and vitrectomy, great progress has been made over the past 30 years in treatment and management of proliferative diabetic and vitreoretinopathy. Success of reattaching retinal tissue with patients having severe PVR has been reported between 36 and 80% overall (Machemer and Lagua, 1978; Aaberg 1988; Hanneken and Michels, 1988; Fishe et al., 1988; The Silicon Oil Study Group, 1992). Success rates were decreased when eyes had already failed vitrectomy or when anterior membranes were present (Lewis and Aaberg, 1991). In diabetics the prognosis is even worse. When eyes with vitreous hemorrhage and preoperatively attached maculas undergo vitrectomy to remove blood 5 to 17% of eyes are reported to lose light perception and only 40–62% regained visual acuity of 20/200 or better (DRVS 1985 and 1990; Machemer and Blankenship, 1981; Michels et al., 1983; Thompson et al., 1987; Rice et al., 1983). In eyes with traction retinal detachment of the macula 20/200 vision was regained in 21 to 58% and loss of light perception occurred in 11 to 19% (Aaberg 1978; Aaberg and Van Horn, 1978; Hutton et al., 1980; Rice et al., 1983). When retinal detachment was both rhegmatogenous and tractional only 25 to 36% regained 20/200 or better vision and loss of light perception ranged from 9 to 23%.

In order to repair retinal detachments caused by PDR and PVR the surgeon must relieve traction and close all breaks. Some residual traction outside the macula is acceptable provided that it does not prevent the surgeon from closing a break. During vitreoretinal surgery, FVMs are removed from the surface of the retina by careful mechanical dissection. The surgeon has several tools at his or her disposal to aid in the removal of fibrovascular tissue from the retina. These tools include various scissors, knives, picks, forceps and other cutting devices (e.g. vitrector). This process is tedious, time consuming and very labor-intensive. Further, mechanical dissection exerts traction on the retina and can lead to complications like hemorrhage, resulting in the formation of a retinal hole, failure to remove enough of the FVM tissue or failure to close a retinal break.

Many of these complications are a direct result of the mechanical nature of the dissection of FVMs. For example cutting FVMs with scissors often results in bleeding which reduces visibility and results in clot formation. The clots can adhere to the surface of the retina and FVMs and cause traction or reduce visibility. To control bleeding requires that the surgeon elevate the intraocular pressure and slowly lower it back to normal while waiting for the bleeding to stop. The surgeon must usually change instruments to clear the hemorrhage before resuming the operation. Also, a retinal break sometimes forms when adherent FVMs are removed from the delicate retinal surface. When this happens all traction near the break must be relieved, the break must be marked and treated with a laser once the retina is reattached. These complications can occur numerous times during the course of a single surgery adding to the time required to complete the procedure. Increased surgical time results in increased fatigue, increased risk of surgical error, increased risk of surgical failure, increased need for re-operation, increased likelihood of severe vision loss, and increased cost to the healthcare system and society. Further, there is an increased risk to the patient from the prolonged exposures to general anesthesia.

Many types of lasers have been tried in the search for more effective means of removing membranes from the surface of the retina including Excimer (ArF), Carbon Dioxide $CO_2$, Holmium:YAG, Erbium:YAG, and other infrared lasers (Hemo et al., 1997; Lewis et al., 1992; Palanker et al., 1994; Tsubota 1990; Peyman and Katoh, 1987; D'Amico et al., 1994; Bende et al., 1989; Walsh et al., 1989; Cummings and Walsh 1993 Karlin et al., 1986; Bridges et al., 1983; Meyers et al., 1983; Miller et al., 1980; Borirakchanyavat et al., 1991;). However, to date laser systems and methods have not been discovered which are suitable for routine laser assisted vitreoretinal surgery.

The Excimer laser, or argon fluoride laser, with a wavelength of 193 nm has been evaluated for vitreoretinal surgery in both air and fluid filled eyes (Hemo et al., 1997; Lewis et al., 1992; Palanker et al., 1994). The Excimer laser is capable of extremely precise ablation of retinal tissue with apparently few complications. However, difficulties with size, cost, maintenance, delivery systems and possible mutagenicity of ultra violet wavelengths have hampered development of Excimer and other similar lasers for vitreoretinal surgery (Pellin et al., 1985; Marshall and Sliney, 1986).

Because of the numerous shortcomings of the currently available laser systems and methods, what is needed is a laser system and method which allows vitreoretinal surgeons to cut and cauterize FVMs while reducing traction on the retina and also removing adherent FVMs by ablation.

SUMMARY

The instant invention is directed to a system for and method of treating a target area of biological tissue with laser radiation. Preferably, the biological tissue is ophthalmic tissue having one or more FVMs on or under the retinal surface of a human eye. Preferably, the FVM is categorized prior to treating the ophthalmic tissue with the laser radiation, wherein separations between underlying retinal tissue and the FVMs, the thickness of FVMs, and the nature of the attachments of FVMs, are determined or characterized prior to laser treatment. The laser assisted vitreoretinal surgery is then tailored to minimize the potential for damage to healthy ocular tissue surrounding the membranes. Variables that can be adjusted in order to tailor the laser assisted vitreoretinal surgery, include but are not limited to the laser sequence (burst and/or pulse sequence), the laser power, the endo-probe configuration(s) used and/or the presentation angles selected to treat and/or dissect the membranes.

In a preferred method of the instant invention, the separations of the FVM(s) from the underlying retinal tissue can be optically measured using a microscope and the laser power can be adjusted to have an effective penetration depth that is less than or equal to the separation of the FVM(s) from the underlying retinal tissue. The effective penetration depth of a laser pulse sequence and optical configuration used can be estimated by measuring the penetration depth of the laser radiation in saline solution or other material having similar absorption properties to the ophthalmic tissue to be treated. During the laser treatment of the ophthalmic tissue, the laser penetration depth can be controlled by adjusting the approach angle, the distance between emitted laser light, the laser pulse sequence and/or power. Further, the endo-probes used to deliver the laser radiation to the ophthalmic tissue during the procedure are preferably tested with a radiation sensitive means prior to dissecting one or more of the FVMs.

Preferably, laser light is delivered to the target area in a sequence of laser bursts. The laser bursts are preferably repeated with a repetition rate of 5.0 KHz or less and are more preferably repeated with a repetition rate in a range of 40 to 10 Hz. The laser pulses delivered to the tissue preferably have laser fluences that are in a range of 1.0 to 10 J/cm$^2$ per pulse and are more preferably in a range of 2.0 to 7.0 J/cm$^2$ per pulse. Each laser burst preferably comprises 2 to 20 laser pulses and more preferably comprises 4 to 12 laser pulses. The laser pulses are preferably separated by less than 2.0 milliseconds and are more preferably separated by 0.01 to 1.25 milliseconds. Further, the laser pulse widths are preferably less than 100 microseconds and more preferably are within a range of 65 to 95 microseconds. The particular laser pulse and sequence that is chosen will depend on the nature of the tissue being treated and the intended outcome. In some instances it is preferable to vary laser pulse and sequence over the course of the procedure.

During laser assisted vitreoretinal surgery, laser radiation is delivered to the target area with exposure spot sizes that are preferably less than 300 microns and are more preferably in a range of 50 to 225 microns. The laser radiation preferably has an effective penetration depth of less than 1.5 mm, wherein the effective penetration depth corresponds to a distance at which 90% of the laser energy is absorbed. The effective penetration depth of the laser radiation can be estimated by measuring the penetration depth of the laser radiation in a saline solution, such as an infusion fluid used to flush the surgical region around the eye during the surgery.

A system for treating FVMs or other tissue(s), in accordance with the instant invention, comprises a laser source for generating laser radiation with a laser sequence, as described above. Preferably, the laser source comprises one or more Er:YAG laser sources for generating laser light with a wavelength of 2.94 microns. The laser pulse length and/or sequence is preferably selectable from a control panel, wherein bursts of laser light preferably comprise a plurality of laser pulses having laser fluences sufficient to cut the tissue without causing significant hemorrhaging to surrounding tissues (viz. causes the surrounding tissue to coagulate).

The laser system preferably has an applicator and/or an optical configuration for delivering laser radiation to the target area during laser assisted vitreoretinal surgery. The optical configuration preferably comprises a delivery optical fiber for emitting the laser light onto the target area of the ophthalmic tissue. The delivery optical fiber is preferably a sapphire or fuse-silica optical fiber with a firing end having a diameter of 500 microns or less and more preferably having a diameter in a range of 50 to 225 microns. However, with the appropriate adjustments to the laser power and laser pulses, optical fibers with firing ends having diameters of 1.0 millimeter or greater are contemplated. The laser source is preferably coupled to the delivery optical fiber through a "matched trunk fiber" configured for focusing the laser light into the delivery optical fiber. The matched trunk optical fiber is preferably a sapphire trunk optical fiber.

The delivery optical fiber is preferably housed within a hand-held endo-probe. The endo-probe is configured to guide the firing end of the delivery optical fiber near to the target area of FVMs or other tissue on the back surface of an eye. Preferably, the endo-probe is configured to guide the firing end of the delivery optical fiber near the target area at preferred angles such that FVMs can be selectively cut and removed from the back surface of the eye.

In yet further embodiments of the instant invention, the delivery optical fiber is a side-firing optical fiber and/or the endo-probe housing is configured with a shielding feature to control, block or filter radiation emitted in unwanted directions from the delivery fiber.

DETAILED DESCRIPTION OF A PREFERRED EMBODIMENT

Figure 1:
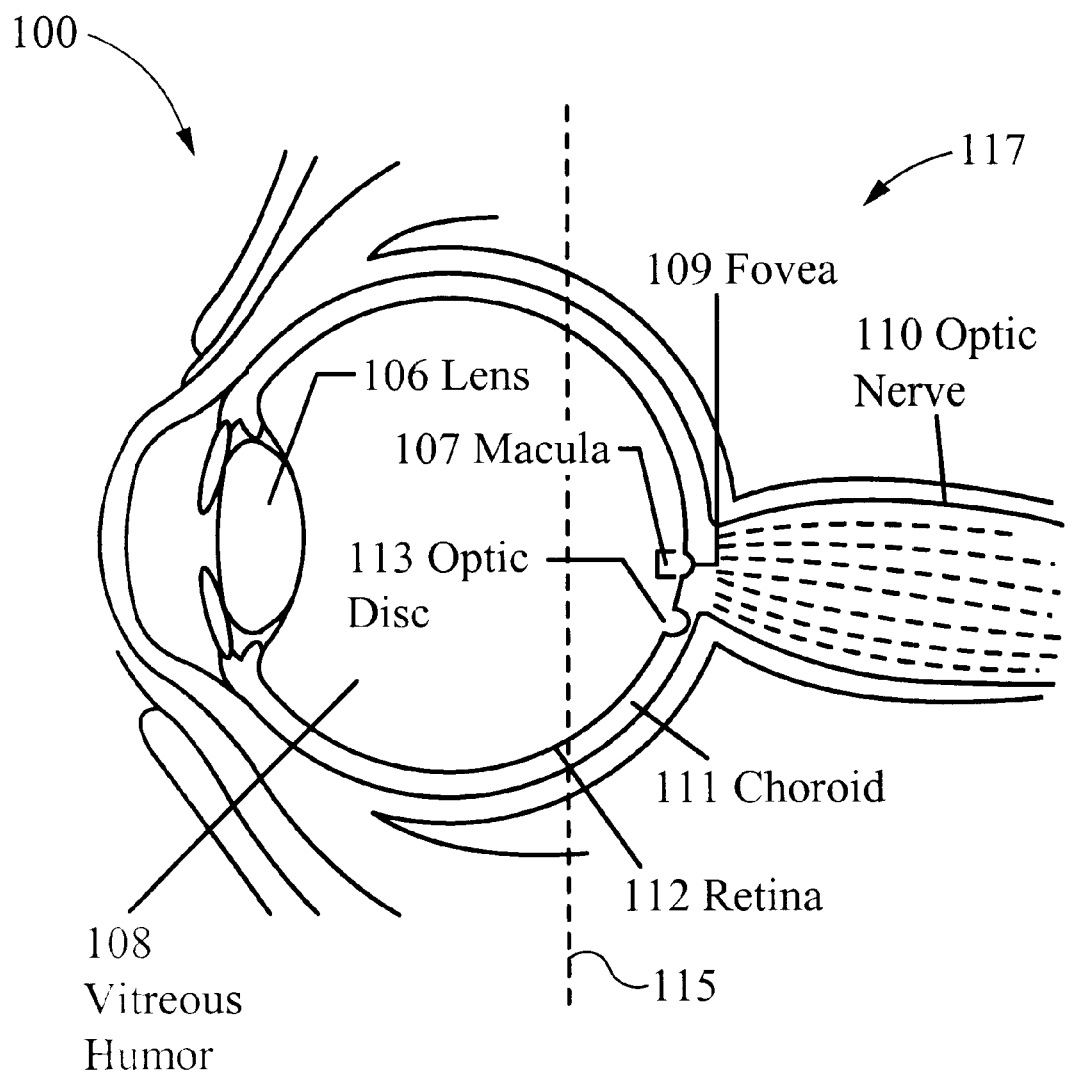
FIG. 1 illustrates a schematic representation of a human eye.

Since most biological tissues contain significant amounts of water and since water strongly absorbs in certain narrow wavelength regions in the mid-infrared region of the spectrum, there has been a strong interest in lasers emitting in this region of the spectrum as an alternative to lasers emitting in the UV region of the spectrum (Peyman and Katoh, 1987; D'Amico et al., 1994; Bende et al., 1989;

Walsh et al., 1989; Cummings and Walsh 1993 Karlin et al., 1986; Bridges et al., 1983; Meyers et al., 1983; Miller et al., 1980; Borirakchanyavat et al., 1991). The Erbium laser is attractive for its low cost, size, simplicity, and reliability.

The wavelength of the Erbium:YAG laser is 2.94 um and corresponds to one of the absorption peaks of water (Assolini et al., 1997; Hale and Querry, 1973; Walsh and Cummings, 1994). Since water is the principal chromophore of the Erbium:YAG laser, it has a relatively short penetration depth in aqueous medium and a high absorption in tissues that contain significant amounts of water. Because of the relatively short penetration depth in aqueous median (approximately 1 micron), radiant energy from the Erbium:YAG laser will generally not travel far once a membrane has been cut; when the membrane is cut in an aqueous environment. These factors make the selectable pulse length Erbium:YAG laser a good device for providing laser radiation to ablate, dissect and/or remove FVMs in laser assisted vitreoretinal surgery or in other similar procedures for laser treatment of other biological tissues, especially biological tissues which are enclosed or are within a cavity of the body.

A selectable pulse length Erbium:YAG laser can enable the surgeon to eliminate extra steps and reduce the risk of complications associated with conventional vitreoretinal surgery involving mechanical dissection. This advantage comes from the fact that the laser may allow the surgeon to cut and coagulate fibrovascular scar tissue in a single step as compared to three or four separate steps required by conventional vitreoretinal surgery. By eliminating steps required to control and clean unwanted hemorrhages, a surgeon can decrease the number of times the back portion of the eye is accessed and exited with a surgical instrument and hence reduce the risk of retinal tears near the vitreous base. Time saved by reducing the incidence of intraoperative hemorrhage can shorten total duration of the procedure, reduce surgeon fatigue and reduce the risk of post-operative complications, including complications that can result from time under anesthesia. Reducing the incidence of post-operative hemorrhage could also help decrease morbidity, shorten recovery time, and decrease the number of primary failures.

Another potential advantage of using a selectable pulse length Erbium:YAG laser to dissect fibrovascular scar tissue over conventional techniques is that the Erbium laser may provide surgeons with a tractionless (atraumatic) method of cutting fibrovascular scar tissue dissection. Traction or tension is unavoidable with conventional methods of surgery and can cause retinal hole formation, hemorrhage and trauma to the retinal cells and nerve fiber layer. All of these complications can negatively impact a patient's ability to recover vision and prolong the recovery period.

The terms ablate and cut are distinguished herein by the aspect ratio of the injury created by the laser beam. Aspect ratio is defined as the ratio of the laser spot diameter to the depth of injury. In the application of the Erbium laser for skin surgery, the laser is said to operate in the ablate mode if the aspect ratio is greater than 10. In general this mode tends to use larger spot sizes relative to depth for tissue penetration of each pulse, thus allowing the surgeon to remove large areas of tissue with a single pulse. The typical spot sizes for ablation in skin resurfacing are 2 to 4 mm with a depth of injury of approximately 100 microns per pulse giving an aspect ratio of greater than 10. The cut mode has an aspect ratio of less than 10. In general, cutting is performed with a laser spot size less than or equal to 300 microns with the same depth of penetration and energy settings per pulse as in the ablation mode, giving an aspect ratio less than 10.

FIG. 1 shows a schematic cross-sectional view of a human eye 100. Detachment and other diseases of the retina 112 can be treated with laser radiation that travels through the lens 106 and the vitreous humor 108 using a focusing lens and a suitable laser source, typically a red or green laser source (diode or Argon). The Fovea 109, which is located in the macula 107, where the receptors for central vision are located. Information is transmitted from the macula 107 into the optic disc 113 and into the optic nerve 110. Proliferative diabetic retinopathy (PDR) and other proliferative or degenerative diseases of the retina 112 lead to the development of FVMs on or under the surface of the retina 112. The development of FVMs and/or scar tissue on or under the surface of the retina 112 can result in the complete loss of vision and/or retinal detachment. Treatment usually involves mechanically cutting the membranes from or dissecting the membranes from the back region of the eye 117 as indicated by the dotted line 115. The procedure is invasive, time consuming and has numerous complications, as previously described.

The current invention is directed to a method for performing vitreoretinal surgery using a laser source to cut or remove fibrous vascular tissue from the back portion 117 of the eye 100. The laser source is preferably a selectable pulse length Erbium:YAG laser which generates laser radiation with a wavelength of 2.94. In accordance with the method of the invention, the laser radiation is used to cut adhesions between fibrovascular scar tissue (not shown) and the retina 112. The laser radiation is preferably applied directly onto the back of the eye 117 using a delivery optical fiber having a diameter of less than 300 microns and more preferably having a diameter in a range of 50 to 225 microns.

Figure 2:
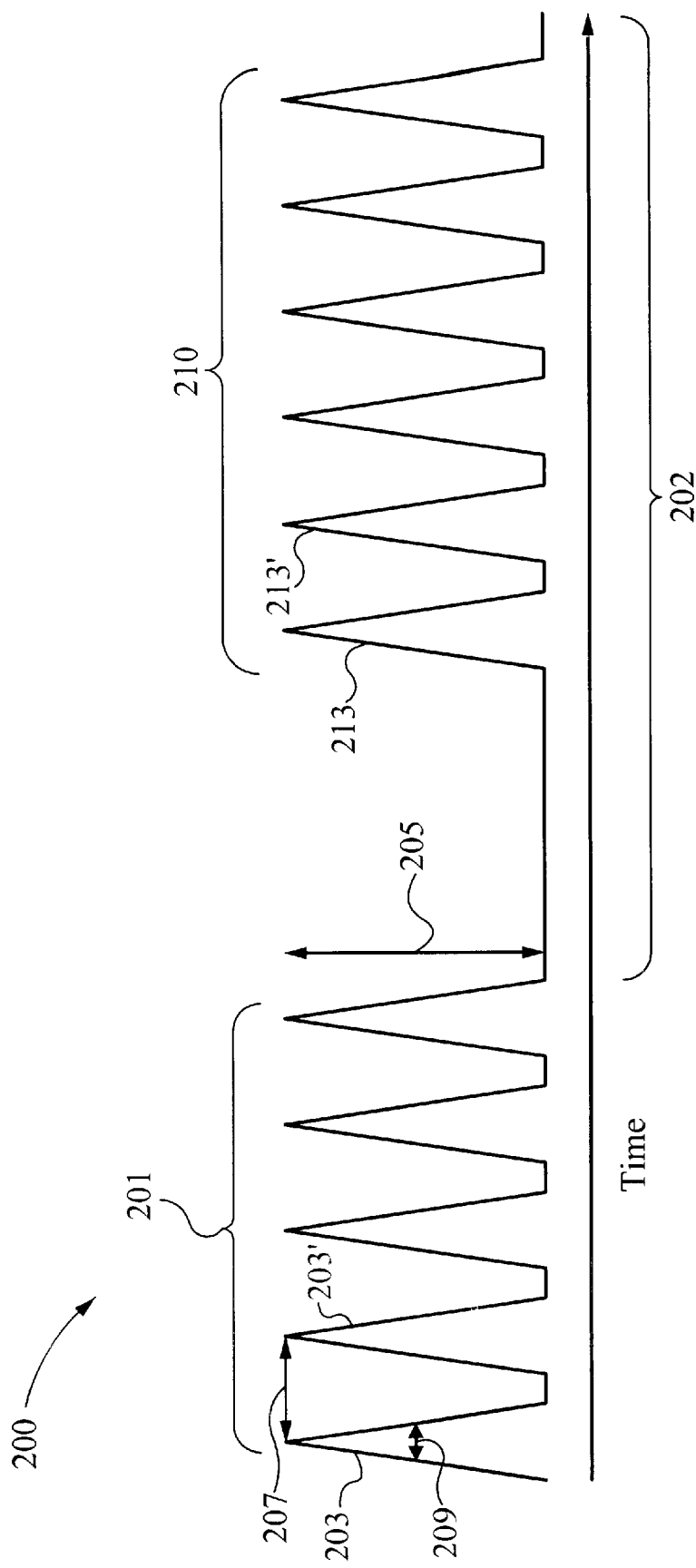
FIG. 2 illustrates a schematic representation of a laser burst comprising a plurality of laser pulses, in accordance with the instant invention.

FIG. 2 shows a schematic representation of a time dependent laser sequence, in accordance with the instant invention. The laser sequence comprises laser bursts 201 and 210 that are preferably generated at a repetition period 202 corresponding to a range in rate of 50 to 10 Hz and more preferably a range of 40 to 10 Hz. Higher repetition rates which can allow for the ability to cut ophthalmic tissues at faster rates are contemplated in the instant invention.

Preferably, each sequential laser burst 201 and 210 comprises a plurality of laser pulses 203 and 203' and 213 and 213'. Each laser burst 201 and 210 preferably comprises 2–24 laser pulses. Sequential laser bursts 201 and 210 can be symmetrical, having the same number of laser pulses per burst or, alternatively, can be asymmetrical, having a range of laser pulses per burst.

The laser radiation used to provide the laser sequence is preferably generated with an energy in a range or 0.5–200 mJ, more preferably generated with an energy around 100 mJ per burst and with laser fluences of 1.0 to 10 J/cm² per pulse, depending on the diameter and construction of the optical fiber(s) used. Most preferably, fluences are generated in a range of 2.0 to 7.0 J/cm² per pulse using an optical fiber having a diameter in a range of 50 to 225 microns.

Still referring to FIG. 2, the laser pulses 203 and 203' and the laser pulses 213 and 213' are preferably separated by a time 207 of less than 2.0 milliseconds and are more preferably separated by a time 207 in a range of 0.01 and 1.25 milliseconds, depending on the nature of tissue to be cut and or coagulated. The laser pulses 203 and 203' preferably have pulse widths 209 of less than 100 microseconds and more preferably have pulse widths 209 in a range of 65 to 95 microseconds.

With the exception of the laser method and system described herein, other operative procedures for the laser assisted vitreoretinal surgery, can be similar to those used for more traditional vitreoretinal surgery. The following example is used for illustrative purposes only and any number of other pre-operative, operative and post-operative procedures are considered to be within the scope of the invention. A patient can be placed under general anesthesia or local anesthesia. Local anesthesia can be administered a 50:50 mixture of 0.75% marcaine and 2% lidocaine (approximately 5 cc) to either the retrobulbar or the peribulbar. Vital signs are preferably monitored continuously during the procedure by a qualified person, such as a hospital anesthesiologist, regardless of the type of anesthesia used.

The operative eye is preferably dilated preoperatively with a pharmacologic agent (e.g., 1% cyclogel, 0.25% hyoscine and 1% mydriacyl). Generally, 1 drop of each will be administered every ten minutes for 3 times until the eye is fully dilated. In some cases, where the eye does not fully dilate with medication, a retractor is necessary to fully expand the pupil.

The surgical region around the operative eye is prepared using a standard three port procedure. Briefly, the operative eye is treated with a betadine solution and sterilely draped so that only the eye is exposed to the operative field. A Williams eyelid speculum can be used to hold the eyelids open. Conjunctiva can be opened at the limbus using 0.3 forceps and Wescott scissors in the temporal and superonasal quadrants. Bipolar cautery can then be used to control conjunctival and episcleral bleeding. Approximately 6.0 vicryl sutures can be passed through partial thickness sclera and limbal tissue and used to secure a lens ring. A 7.0 vicryl suture can be used to secure the infusion line in the inferotemporal quadrant 3.5 to 4.0 mm posterior to the limbus.

The eye is preferably flushed with an infusion fluid during the operation. The infusion fluid is a physiologically buffered saline solution, such as that used for conventional pars plana vitrectomies. Additional sclerotomies for right and left-hand instruments are preferably placed at or about the two and eleven o'clock meridians 3.5 to 4.0 mm posterior to the limbus using a 19 or 20 gauge blade.

Intraocular viewing can be provided by an operating microscope that includes an indirect viewing system (Volk or Biom) and a direct viewing system (e.g. Landers contact lens viewing system). The operating microscope is equipped with side arms to accommodate a video camera and observer oculars for a surgical assistant. Video camera monitor and tape may be used to record the operation.

Figure 3A:
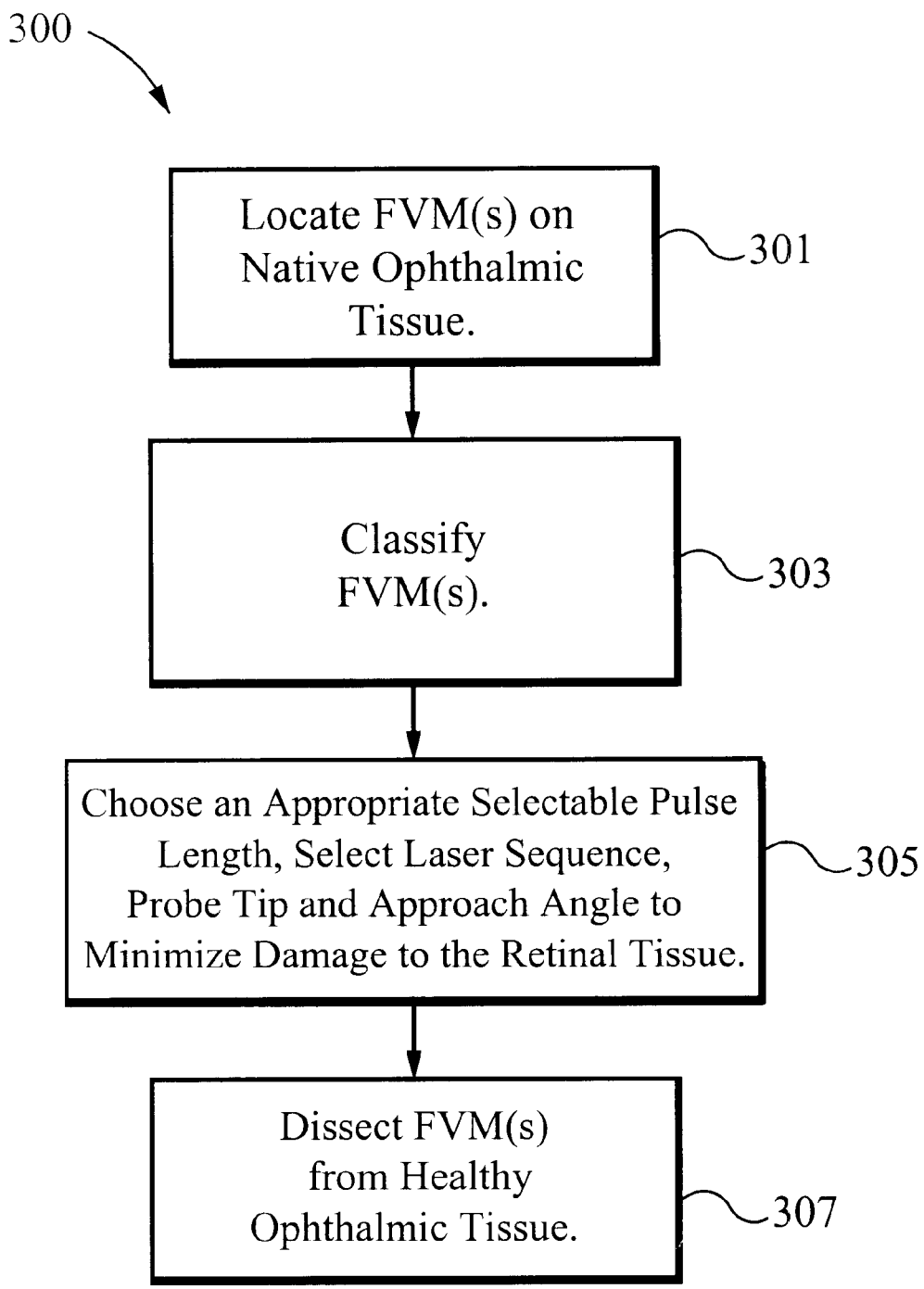
FIG. 3a shows a block diagram outlining steps for treating fibrous vascular tissue, in accordance with the method of the instant invention.

Now referring to FIG. 3a, once the view of the retina tissue is optimized using a microscope system such as the one described above, then in the step 301, FVMs are located. After the FVMs are located in the step 301, then in the step 303 the membranes are preferably classified or characterized. The FVMs are preferably classified or characterized by their thicknesses, their separations from the retinal tissue underneath and the type of membrane tissue that is present (viz. the nature of the attachments of the membranes to the surrounding ophthalmic tissue).

The thicknesses of the membranes and the separations of the membranes from the retinal surface is readily accessed by inspection using the operating microscope system, such as the one described above. Sheet membranes, typically referred to as S-FVMs, stretch across the surface of the retina and exert traction at focal points of attachment that can be dislocated using a dissection technique referred to as segmentation. Plaque membranes, on the other hand, typically referred to as P-FVMs, have multiple points of attachment to retinal blood vessels spaced very close together. The traction appears to be over a broad region of the retina. These membranes can not be removed by segmentation and are usually dislocated using a delamination technique. Depending on the thicknesses of the membranes, the separations of the membranes from the retinal surface and nature of the attachment of the membrane to the surrounding tissues, an operative strategy is developed in the step 305, wherein an appropriate selectable pulse length, laser sequence and approach angle is chosen to minimize damage to the retinal tissue.

One of the most important considerations in developing an operative strategy includes ensuring that there is minimal damage to the retinal tissue. Accordingly, the laser sequence and approach angles used to treat the membrane are preferably tailored to achieve this goal. For example, since most FVMs can be treated with an effective penetration depth of less than 1.5 mm, preferably the laser sequence used is selected to have an effective penetration depth of 1.5 mm or less. The effective penetration depth is herein referred to as the distance at which 90% of the laser light is absorbed in an aqueous solution, such as infusion fluid used during the procedure described above, a biological tissue being treated with the laser light and/or a combination thereof. Accordingly, when the target membrane is greater than 1.0 mm from the underlying retinal tissue and if the target membrane is not too thick (150 microns or less) then the laser radiation can be applied with an approach angle that is approximately normal to the retinal surface tissue in order to minimize the time required to dissect the membrane in a process referred to herein as segmentation or delamination. During segmentation the surgeon relieves traction by making numerous vertical cuts between the points of attachment of the fibrovascular scar tissue to the retina. The actual attachments are not necessarily cut and, therefore, the fibrovascular membrane is not necessarily completely removed. However, if the membrane is located 1.0 mm or less from the retinal surface and the membrane is relatively thick (150 microns or greater), the approach angle for the application of laser radiation is preferably parallel with the retinal surface or any angle directing the laser radiation upward away from the retinal surface in a process referred to herein as delamination. During delamination the actual points of attachment between the fibrovascular scar tissue and the retina are cut. Surgeons use either or both techniques to relieve traction and reattach the retina. Typically, membranes that are classified as plaque have positions of attachment, or close attachment, to the retinal tissue and, therefore need to be removed with laser radiation very near parallel with the retinal surface in the delamination process. In many cases a combination of angles, laser sequences (both burst and pulse parameters), and endo-probes are required for segmentation and delamination in a single operation.

Figure 3B:
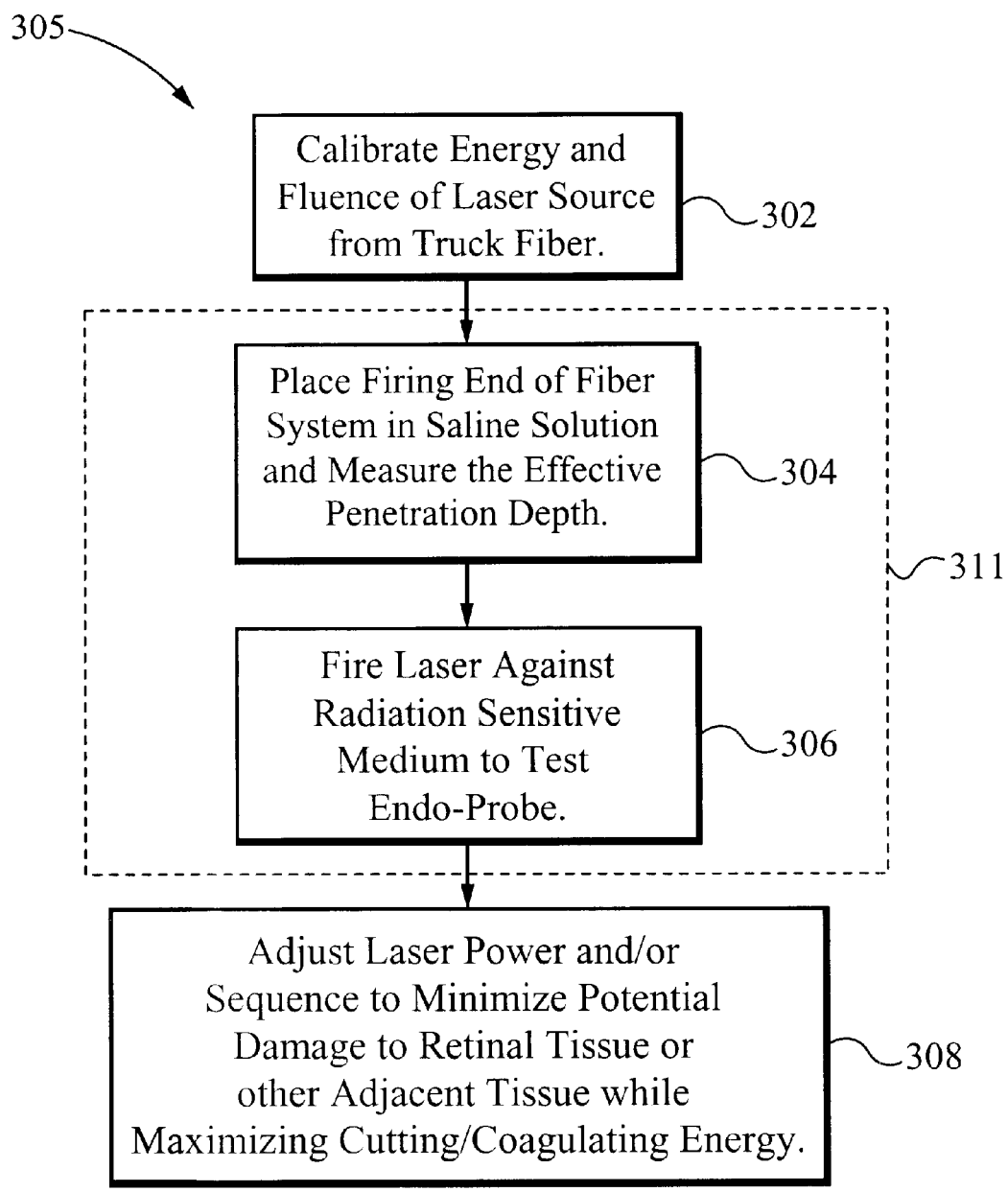
FIG. 3b shows a block diagram outlining steps for pre-selecting laser radiation and endo-probes, in accordance with the instant invention.

In order to further ensure the safety of the patient and the success of the laser assisted vitreoretinal surgery, prior to the step 307 of dissecting or cutting the membrane, the optical configuration and the laser sequence is preferably tested in the steps outlined in the block diagram 305, as shown in FIG. 3b.

Referring now to FIG. 3b, in the step 302 the energy and fluence of the laser radiation is preferably calibrated from the end of a trunk fiber configured to transmit the laser radiation into a delivery fiber, described in detail below. Calibration of energy and fluence are measured with an optical power meter, such as a D30MM optical power meter, available from ThorLabs (Newton, N.J.). The use and operation of optical power meters is known. Briefly, the D30MM optical power meter uses a thermal pile to generate an electrical signal that is amplified and a Fluke Multimeter Type 79111 measures the output. The thermal pile and amplifier are calibrated and traceable to NIST standards. The spectral response at 250 nm to 10.6 nm has an accuracy that is better than +/−5%. With the amplifier set at a gain of 1000 the conversion is 0.1V/watt, the energy and fluence is calculated using the laser output energy, transmission, the number of pulses per burst, the burst repetition rate and the diameter of the fiber.

After, the energy and fluence of the laser are calibrated in the step 302, then in the step 311, the endo-probe is calibrated and tested. For example, in the step 304 an endo-probe with a delivery fiber is coupled to the trunk fiber. In the step 306, the firing end of the delivery probe is tested by exposing a piece of thermally sensitive fax paper (such as Thermal Fax paper; 3M) to radiation emitted from the firing end of the delivery optical fiber. A working endo-probe should transmit laser radiation through the firing end of the delivery optical fiber which corresponds to approximately 0.1 mJ/burst and which consistently produces a visible burn on the test paper. The energy for visible damage to thermal test paper has been measured to be 0.04 mJ/pulse, which is considerably lower than the threshold of retinal tissue damage. Therefore, the thermal sensitive paper is useful for testing the gross operation of the endo-probe used as well as the distribution of radiation and effectiveness of safety features of the endo-probe, described in detail below.

After the endo-probe is calibrated and tested in the step 311, then in step 308, the laser power and/or sequence can be adjusted to minimize potential damage to the retina taking into consideration the separation of the membrane(s) from the retinal surface, thicknesses of the membranes and the nature of the attachment(s) to the surrounding ophthalmic tissue, as determined in the step 303.

The laser power and the firing sequence of the laser is preferably selected such that the effective penetration distance within the target tissues is 1.5 mm or less. The effective penetration distance can be determined by empirical methods, which can include measuring the absorption characteristics of the laser light in the target tissue or other similar tissue.

Figure 4:
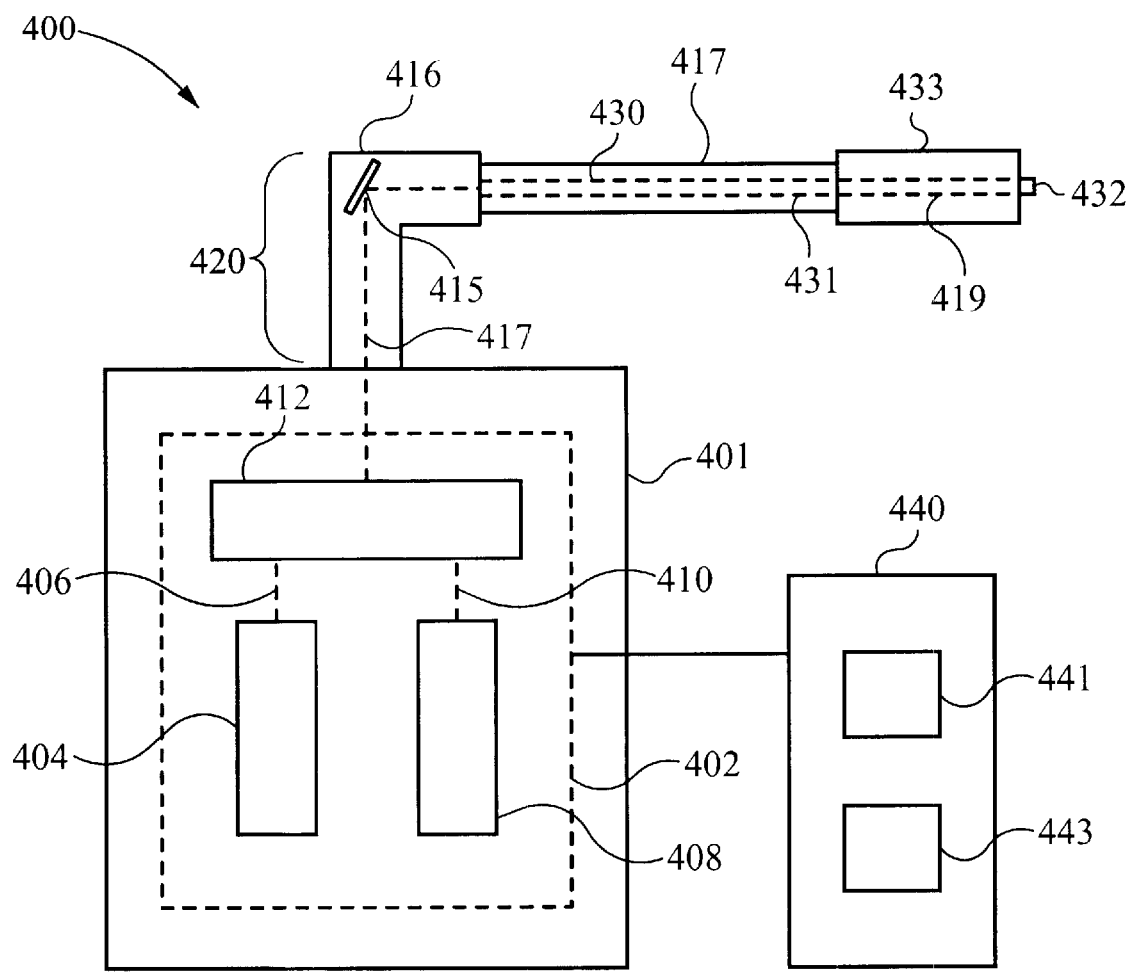
FIG. 4 illustrates a laser system for treating ophthalmic tissue, in accordance with the instant invention.

FIG. 4 illustrates a system 400 in accordance with a preferred embodiment of the instant invention. The system 400 of the instant invention is configured to generate a laser sequence such as described above for use in laser assisted vitreoretinal surgery. However, the system 400 of the instant invention is contemplated to have applications for the treatment of any number of vascular tissues. The laser system 400 preferably comprises a system housing 401 that includes a laser source 402 for generating a single laser output beam 417. The laser source 402 preferably includes two Erbium:YAG lasers 404 and 408 which generate the laser beams 406 and 410, respectively. The laser beams 406 and 410 are preferably combined into the single laser output beam 417 having the same wavelength as the beams 406 and 410, using a galvanometer 412, wherein the galvanometer preferably alternates between the laser outputs 406 and 410 to produce the single output beam 417.

The system 400 also preferably includes an optical configuration 420 for directing the output laser beam 417 onto a target ophthalmic tissue. The optical configuration 420 is preferably very flexible to allow the surgeon to position the laser in any number of locations during an operation. The optical configuration 420 can include a housing 416 for housing and holding directing optics 416. Directing optics 416 can include but are not limited to, mirrors, lenses and fibers. Preferably, the optical configuration 420 comprises one or more flexible trunk fibers 430 within a fiber sleeve 417. The one or more flexible trunk fibers 430 preferably comprises a trunk fiber with a diameter between 200 to 500 microns which is configured to transmit laser radiation from the output beam 417 into one or more delivery fibers 419.

The one or more delivery optical fibers 419 preferably comprise a sapphire or fused silica (glass) fiber with a diameter of less than 500 microns and more preferably with a diameter in a range of 50 to 225 microns. The one or more delivery optical fibers 419 are preferably very flexible and can bend through small angles. The one or more delivery optical fibers 419 are preferably coated with gold or other suitable material which can provide stabilization as the fibers are bent through small bending radii and which can also help to reduce light loss through the fiber walls.

Preferably, the delivery fiber 419 passes through a flexible housing 433 which allows the surgeon to manipulate the firing end 432 of the delivery fiber 419 during laser assisted vitreoretinal surgery. The flexibility of the housing 433 allows the surgeon to readily change the approach angle of the delivery fiber 419 during laser surgery without having to change the probes.

In further embodiments of the invention, the system 400 comprises a interface 440 coupled to the laser source 402 for selectively controlling the power and pulse sequence of the output laser beam 417. In use, a surgeon can select a laser sequence and pulse length from a set of predetermined laser sequences comprising laser bursts and pulses, as previously described, from a first control 441. Preferably, the surgeon can also adjust the power or laser transmission delivered through the firing end 432 of the delivery fiber 419, from a second control 443. Accordingly, the surgeon can modify the laser therapy during the surgical procedure.

In order to facilitate the number of approach angles available to the surgeon during the operation, and to further reduce the potential for damage to the retinal tissue during the procedure, the system is preferably configured to have a set of interchangeable endo-probes, such as described in detail below.

Figure 5A:
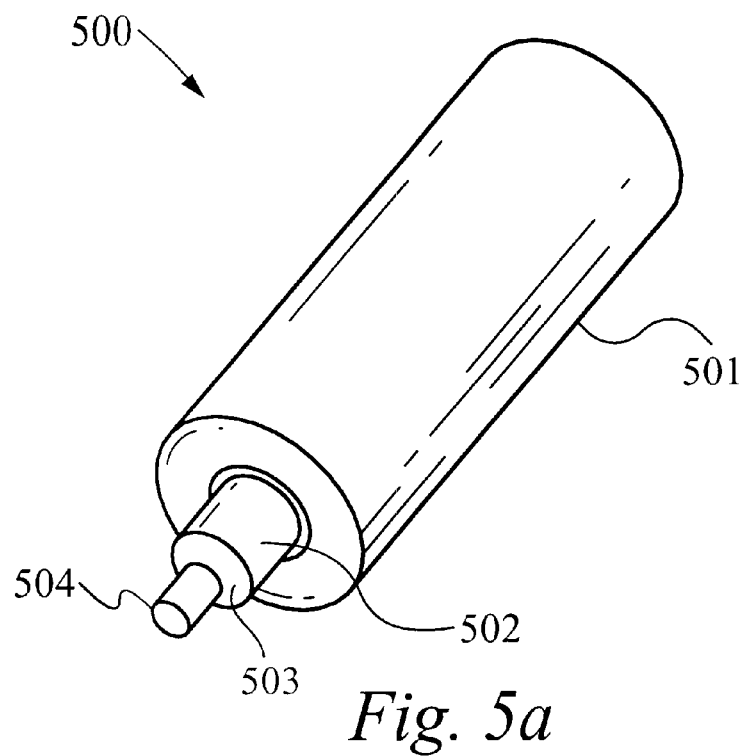
FIGS. 5a–d illustrate perspective views of endo-probe configurations, in accordance with the instant invention.

Referring to FIG. 5a, in accordance with the instant invention an endo-probe 500 is configured with a housing 501 for securing and holding an optical fiber structure 502. The firing end 503 of the optical fiber structure 502 preferably extends out of the housing 501 and irradiates laser radiation 504 in a direction that is substantially parallel along the length axis of the optical fiber structure 502. Preferably, the housing 501 is flexible and/or bendable, such that the optical fiber structure 502 can be bent within the housing and thereby allowing laser radiation to be irradiated throughout a range of relative angles.

Figure 5B:
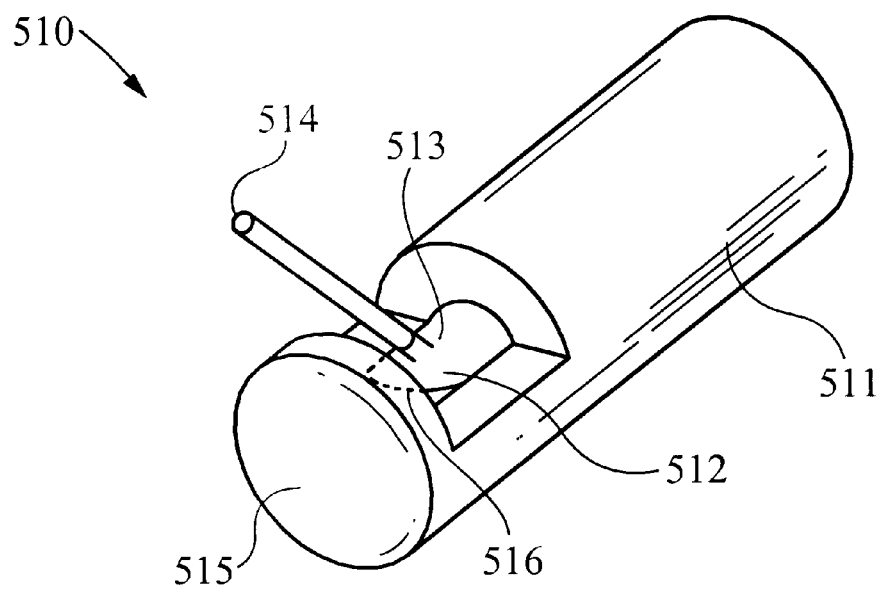

FIG. 5b shows an alternative endo-probe construction 510. In accordance with this embodiment, the endo-probe 510 has a housing 511 for holding an optical fiber structure 512. The optical fiber structure 512 has a beveled region 516 that is beveled to an angle of approximately 30 to 45 degrees relative to the axis of the optical fiber structure 512. The preferred angle of the beveled region 516 can depend on the media or medium in which the laser is being operated (e.g. air versus liquid). In accordance with this embodiment, laser radiation 514 is emitted from a firing region 513 on the optical fiber that is opposite the beveled region 516 and at an angle relative to the axis of the optical fiber structure 512, as determined by the angle of the beveled region 516. The endo-probe construction 510 is particularly useful for providing the surgeon with alternative approach angles during the treatment and/or dissection of FVMs. Preferably, the endo-probe construction 510 is configured with a beam-blocking or shield structure 515 that can be integral with the housing 511, as shown, or alternatively can be separate from the housing 511. The beam-blocking structure 515 blocks unwanted forward propagating laser radiation and/or controls the application of laser radiation during laser assisted vitreoretinal surgery. The housing 511 can be flexible or bendable allowing the approach angle of the laser radiation 514 to be readily changed during the treatment/and or dissection of FVMs.

Figure 5C:
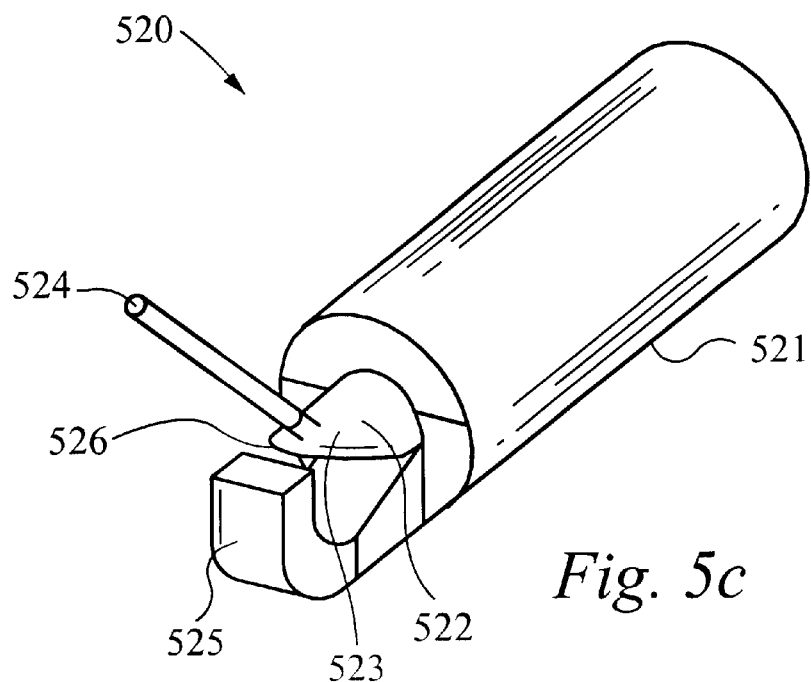

FIG. 5c illustrates an endo-probe construction 520 configured with a bent beam-blocking or shield structure 525. The endo-probe construction 520 has a housing 521 which can be flexible or bendable, as previously explained. The housing 521 holds an optical fiber structure 522 and bends to allow a surgeon to control the approach angle of the laser radiation 524 during the treatment/and or dissection of FVMs. The optical fiber structure 522 has a firing region 523 that preferably emits the laser radiation 524 at an angle relative to the axis of the body of the optical fiber structure 522, as determined by the angle of the beveled region 526 opposite of the firing region 523. The beam-blocking structure 525 curves around the beveled region 526 of the optical fiber structure 522 in order to block unwanted laser radiation during laser assisted vitreoretinal surgery and assists the surgeon in the manipulation of tissue near the tip of the fiber. The optical fiber structure 520, like the optical fiber construction shown in FIG. 5b, allows the surgeon to use different approach angles that otherwise can be difficult to achieve with a straight fiber, such as shown in FIG. 5a.

Figure 5D:
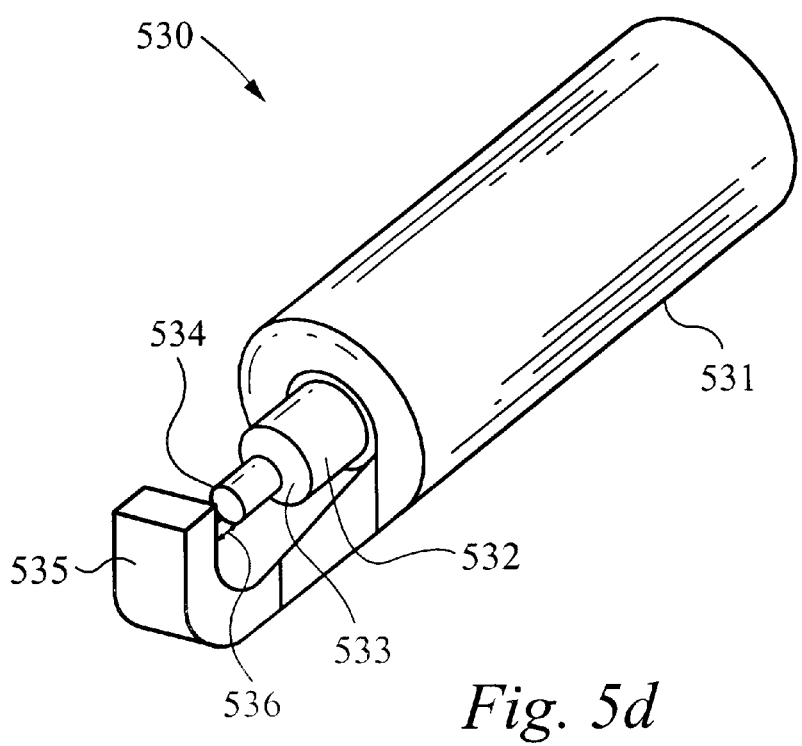

FIG. 5d shows an endo-probe construction 530, in accordance with an alternative embodiment of the instant invention. The endo-probe 530 has a housing 531 for holding an optical fiber structure 532, which is preferably flexible or bendable, such as previously described. The optical fiber structure 532 has a firing end 533 which emits laser radiation 534 in a direction that is substantially parallel with the axis of the body of the optical fiber structure 532. A beam-blocking and/or tissue manipulation feature 535 curves around the firing end 533 of the optical fiber structure 532 such that the beam-blocking and/or tissue manipulation feature 535 and the firing end 533 of the optical fiber form a gap 536 into which the laser radiation 534 is emitted. In use, ophthalmic tissue can be cut by placing the ophthalmic tissue in the gap 536 between the firing end 533 of the optical fiber structure 532 and the beam-blocking feature 535 and exposing the tissue to laser radiation, as previously explained. The beam-blocking structure 535 prevents unwanted laser radiation from exposing surrounding ophthalmic tissue during a cutting procedure.

Figure 6A:
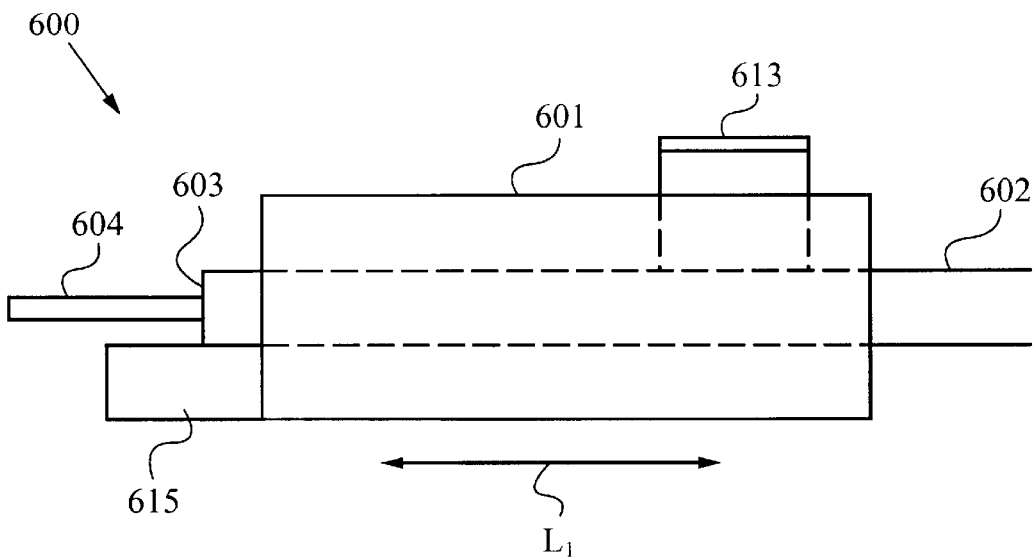
FIGS. 6a–b illustrate perspective views of an endo-probe configuration with an adjustable delivery fiber that is configured to move in and out of a sheath housing, in accordance with the instant invention.
Figure 6B:
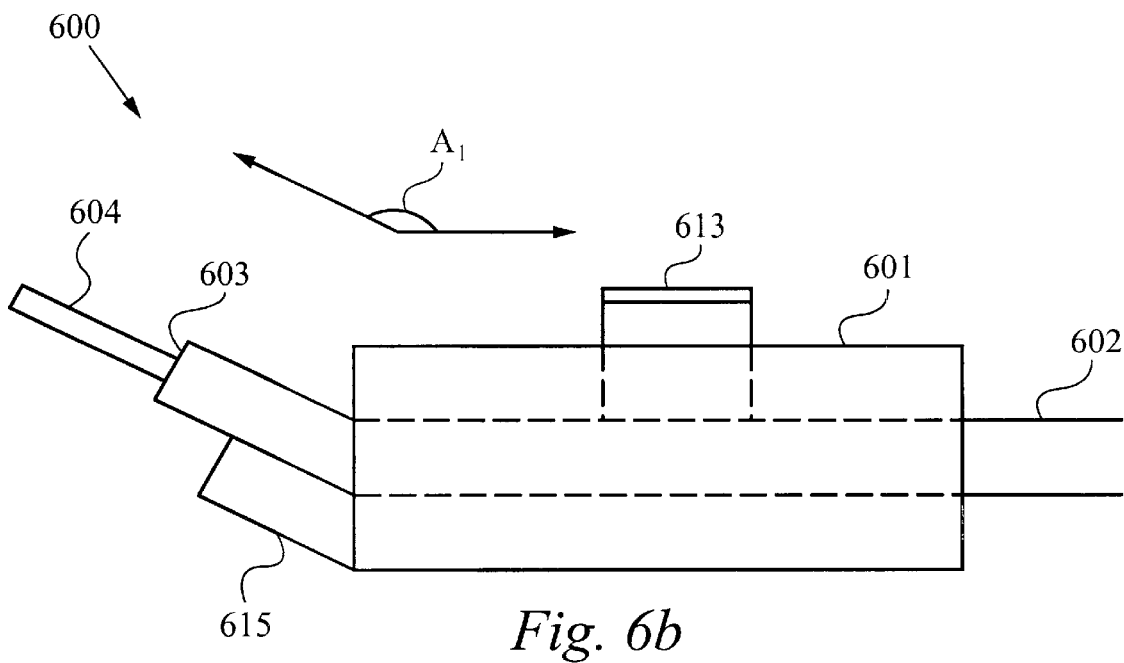

FIGS. 6a–b illustrate an endo-probe 600 in accordance with an alternative embodiment of the instant invention. The endo-probe 600 has an adjustable optical fiber 602 within a shroud structure 601. The adjustment feature of the endo-probe 600 further facilitates the ability to access a variety of approach angles during laser treatment of vascular biological tissues. In accordance with this embodiment, the optical fiber 602 is coupled to an adjustor 613 which allows the optical fiber 602 to be extended from and retracted within the shroud structure 601 along the length $L_1$ of the shroud structure 601. The endo-probe 600 can also be configured with a finger adjustment which allows the firing end 603 of the optical fiber 602 to be adjusted such that laser radiation 604 can be emitted from the endo-probe 600 through a range of angles $A_1$, relative to the length $L_1$ of the shroud structure 601. The shroud structure 601 can be flexible or bendable, as previously explained, to further enhance the ability of the endo-probe 600 to be manipulated within and/or through a cavity within the body.

The method and system of the instant invention provides a versatile laser treatment for preforming laser assisted vitreoretinal surgery and other surgeries that involve the treatment of vascular tissue. The system and method can reduce the number of steps required to perform vitreoretinal surgery, can allow the surgeon to reach tissue for incising or ablating which are not readily accessed by other means and can reduce the potential for damage to healthy ophthalmic tissue, including retinal tissue, while effectively treating FVMs. While the current invention has been described primarily in terms of performing vitreoretinal surgery, the invention is contemplated to have applications in a number of different procedures for the treatment of biological tissues, especially for the treatment of vascular biological tissues, such as cardiovascular tissues, which are within a cavity of the body. Further, the system and method of the instant invention are also believed to be particularly useful for performing choroidal translocation, wherein healthy choroidal tissue is partially dissected from an eye and translated to a degenerative region of the same eye and attached thereto, while remaining partially attached to a natural blood supply.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiment chosen for illustration without departing from the spirit and scope of the invention.

What is claimed is:

1. A method of treating vascular tissue, the method comprising:
   a. locating a target area of the vascular tissue comprising fibrous vascular tissue on or near retinal tissue;
   b. selecting an approach angle; and
   c. delivering laser radiation to the target area at the approach angle such that the laser radiation does not significantly penetrate the retinal tissue at the retinal surface, the laser radiation comprising a sequence of laser bursts, wherein each laser burst comprises a plurality of laser pulses having laser fluences sufficient to cut at least a portion of the fibrous vascular tissue away from the retinal tissue while controlling hemorrhaging.

2. The method of claim 1, wherein the laser bursts are repeated at a repetition rate of 5.0 KHz or less.

3. The method of claim 1, wherein the repetition rate is in a range of 10 to 40 Hz.

4. The method of claim 1, wherein the laser fluences are in a range of 1.0 to 10 J/cm$^2$.

5. The method of claim 1, wherein the laser fluences are in a range of 2.0 to 7.0 J/cm$^2$.

6. The method of claim 1, wherein laser bursts comprise 1–24 pulses.

7. The method of claim 6, wherein the laser pulses are separated by less than 2.0 milliseconds.

8. The method of claim 7, wherein the laser pulses are separated by a time in a range of 0.01 and 1.25 milliseconds.

9. The method of claims 8, wherein the laser pulses have pulse widths of less than 100 microseconds.

10. The method of claim 9, wherein the laser pulses have pulse widths in a range of 65 to 95 microseconds.

11. The method of claim 1, wherein the laser radiation is delivered to the target area with exposure spot sizes of less than 500 microns.

12. The method of claim 11, wherein the exposure spot sizes are in a range of 50 to 225 microns.

13. The method of claim 12, wherein the laser radiation has a penetration depth through an aqueous saline medium of less than 1.5 mm.

14. The method of claim 13, wherein the ratio of the exposure spot sizes to the penetration depth is less than 10:1.

15. The method of claim 1, wherein the laser radiation comprises laser radiation having a wavelength of 2.94 microns and an energy in a range of 5–200 mJ per burst.

16. The method of claim 1, wherein the vascular tissue corresponds to vascular ophthalmic tissue.

17. The method of claim 1, wherein the laser radiation is delivered at a controlled distance from the retinal tissue.

18. A method of removing a fibrous membrane from a retinal surface, the method comprising:
   a. locating the fibrous membrane on the retinal surface; and
   b. delivering laser radiation to the fibrous membrane, the laser radiation comprising a sequence of laser bursts, wherein each laser burst comprises a plurality of laser pulses having laser fluences sufficient to cut the fibrous membrane from the retinal surface while controlling hemorrhaging.

19. The method of claim 18, further comprising determining a separation between a fibrous membrane and the retinal surface and selecting an approach angle for cutting the fibrous vascular tissue such that the laser radiation does not significantly penetrate retinal tissue at or near the retinal surface.

20. A method of laser assisted vitroretinal surgery, the method comprising:
   a. selecting a laser pulse sequence; and
   b. delivering the laser pulse sequence to a back surface of an eye, the laser pulse sequence comprising a sequence of laser bursts, wherein each laser burst comprises a plurality of laser pulses having laser fluences sufficient to cut fibrous tissue away from the back surface of the eye while controlling hemorrhaging.

21. The method of claim 20, wherein the back surface of the eye comprises retinal tissue.

* * * * *